(12) United States Patent
Poree

(10) Patent No.: US 10,639,435 B2
(45) Date of Patent: May 5, 2020

(54) FLOW MEASURING APPARATUS AND INHALATION APPARATUS COMPRISING THE SAME

(71) Applicant: PROTECSOM AMERIQUE DU NORD INC., Drummondville (CA)

(72) Inventor: Thierry Poree, St-Pierre-Eglise (FR)

(73) Assignee: PROTECSOM AMERIQUE DU NORD INC., Drummondville (CA)

( * ) Notice: Subject to any disclaimer, the term of this patent is extended or adjusted under 35 U.S.C. 154(b) by 697 days.

(21) Appl. No.: 14/915,100

(22) PCT Filed: Aug. 28, 2014

(86) PCT No.: PCT/CA2014/000660
§ 371 (c)(1),
(2) Date: Feb. 26, 2016

(87) PCT Pub. No.: WO2015/027326
PCT Pub. Date: Mar. 5, 2015

(65) Prior Publication Data
US 2016/0213865 A1    Jul. 28, 2016

(30) Foreign Application Priority Data

Aug. 30, 2013 (CA) ...................... 2826516

(51) Int. Cl.
*A61M 15/00* (2006.01)
*A61M 16/06* (2006.01)
(Continued)

(52) U.S. Cl.
CPC .... *A61M 15/0065* (2013.01); *A61M 15/0015* (2014.02); *A61M 15/0086* (2013.01);
(Continued)

(58) Field of Classification Search
CPC .......... A61M 15/0016; A61M 15/0018; A61M 15/0021; A61M 15/0065;
(Continued)

(56) References Cited

U.S. PATENT DOCUMENTS 2,270,540 A * 1/1942 Mallory ................. A23C 3/033
165/144
3,045,666 A * 7/1962 Dubsky .................... A61B 5/08
600/538

(Continued)

OTHER PUBLICATIONS

International Search Report dated Nov. 7, 2014 in the corresponding International Patent Application No. PCT/CA2014/000660.

*Primary Examiner* — Kathryn E Ditmer
(74) *Attorney, Agent, or Firm* — Benoit & Côté Inc.; Mathieu Miron

(57) ABSTRACT

The present document describes a flow measuring apparatus for measuring the air flow through a section of an inhalation apparatus, and for measuring the drug delivery by inhalation using an inhalation apparatus. The flow measuring apparatus comprises a set of Pitot tubes configured for traversing entirely the lumen of the section of an inhalation apparatus. The set of Pitot tubes comprises a first and second Pitot tube which are respectively fluidly connected to a differential pressure sensor, for measuring a difference between a stagnation pressure and a static pressure within the flow measuring apparatus.

20 Claims, 5 Drawing Sheets

(51) Int. Cl.
  *A61M 16/04* (2006.01)
  *G01F 1/46* (2006.01)
(52) U.S. Cl.
  CPC .............. *G01F 1/46* (2013.01); *A61M 15/009* (2013.01); *A61M 15/0016* (2014.02); *A61M 15/0018* (2014.02); *A61M 15/0021* (2014.02); *A61M 16/04* (2013.01); *A61M 16/06* (2013.01); *A61M 2205/3334* (2013.01); *A61M 2205/3355* (2013.01); *A61M 2205/502* (2013.01)
(58) Field of Classification Search
  CPC .. A61M 2016/0015; A61M 2016/0018; A61M 2016/003; A61M 2016/0033; A61M 2016/0036; A61M 2016/0039; A61M 2016/0042; A61M 16/003; A61M 2016/0027; G01F 1/46
  See application file for complete search history.

(56) References Cited

U.S. PATENT DOCUMENTS

| | | | | |
|---|---|---|---|---|
| 4,154,100 A * | 5/1979 | Harbaugh | G01F 1/46 | 73/861.66 |
| 4,453,419 A * | 6/1984 | Engelke | G01F 1/46 | 73/861.66 |
| 4,592,239 A * | 6/1986 | Cutler | G01F 1/46 | 73/861.66 |
| 4,624,146 A * | 11/1986 | Nakagawa | G01F 1/46 | 73/861.66 |
| 4,645,242 A * | 2/1987 | Coleman | F16L 41/082 | 285/141.1 |
| 4,703,661 A * | 11/1987 | Evers | G01F 1/46 | 73/861.66 |
| 4,717,159 A * | 1/1988 | Alston | G01F 15/185 | 277/314 |
| 5,036,711 A * | 8/1991 | Good | G01F 1/46 | 73/861.66 |
| 5,038,773 A * | 8/1991 | Norlien | A61B 5/087 | 128/205.23 |
| 5,088,332 A * | 2/1992 | Merilainen | A61B 5/0833 | 600/538 |
| 5,111,827 A * | 5/1992 | Rantala | A61B 5/087 | 600/532 |
| 5,123,288 A * | 6/1992 | Tench | G01P 5/165 | 73/202.5 |
| 5,180,373 A * | 1/1993 | Green | A61B 17/3498 | 251/149.1 |
| 5,303,602 A * | 4/1994 | Morgan | G01F 1/40 | 73/866.5 |
| 5,753,825 A * | 5/1998 | Brandt, Jr. | G01F 1/36 | 73/861.66 |
| 5,794,612 A * | 8/1998 | Wachter | A61M 15/0086 | 128/200.23 |
| 5,817,950 A * | 10/1998 | Wiklund | G01F 1/46 | 73/861.66 |
| 5,969,266 A * | 10/1999 | Mahoney | G01F 1/88 | 73/861.65 |
| 6,044,716 A * | 4/2000 | Yamamoto | G01F 1/40 | 73/716 |
| 6,129,113 A * | 10/2000 | Van Becelaere | F16K 1/165 | 137/557 |
| 6,164,143 A * | 12/2000 | Evans | G01F 1/46 | 73/52 |
| 6,430,996 B1 * | 8/2002 | Anderson | B64D 15/20 | 73/170.26 |
| 6,470,755 B1 * | 10/2002 | Beachey | G01F 1/46 | 73/756 |
| 7,454,267 B2 * | 11/2008 | Bonney | A61M 15/00 | 221/2 |
| 7,478,565 B2 | 1/2009 | Young | | |
| 7,561,056 B2 * | 7/2009 | McMillan | G01F 1/363 | 340/603 |
| 7,779,834 B2 | 8/2010 | Calluaud et al. | | |
| 2003/0205229 A1 * | 11/2003 | Crockford | A61K 38/12 | 128/204.23 |
| 2003/0234015 A1 * | 12/2003 | Bruce | A61M 15/0086 | 128/200.23 |
| 2004/0144383 A1 * | 7/2004 | Thomas | A61M 16/0045 | 128/204.18 |
| 2006/0021620 A1 * | 2/2006 | Calluaud | A61M 16/14 | 128/204.22 |
| 2007/0163598 A1 * | 7/2007 | Chang | A61M 16/022 | 128/207.16 |
| 2007/0261498 A1 * | 11/2007 | Orr | A61B 5/087 | 73/753 |
| 2008/0092898 A1 * | 4/2008 | Schneider | A61B 5/0878 | 128/206.28 |
| 2009/0139517 A1 * | 6/2009 | Wachtel | A61M 15/0028 | 128/200.23 |
| 2011/0079220 A1 * | 4/2011 | Altobelli | A61B 5/08 | 128/200.14 |
| 2011/0270541 A1 * | 11/2011 | Cha | A61B 5/087 | 702/47 |
| 2012/0291781 A1 * | 11/2012 | Kaufmann | A61M 15/008 | 128/203.15 |
| 2015/0191884 A1 * | 7/2015 | Aughton | E02B 7/40 | 405/99 |

* cited by examiner

FLOW MEASURING APPARATUS AND INHALATION APPARATUS COMPRISING THE SAME

CROSS-REFERENCE TO RELATED APPLICATIONS

This application is a US National Phase application under 35 USC § 371 of PCT/CA2014/000660, filed Aug. 28, 2014, which in turn, claims priority and the benefit of Canadian patent application 2,826,516, filed Aug. 30, 2013, the specifications of which are hereby incorporated by reference in their entireties.

BACKGROUND

(a) Field

The subject matter disclosed generally relates to a flow measuring apparatus and inhalations apparatus for drug delivery by inhalation comprising the same.

(b) Related Prior Art

Many drugs to treat diseases such as obstructive pulmonary disease, asthma, bronchial, or the bronchiolitis, are administered by inhalation for example by means of metered dose inhalers (MDI). The inhaler uses a propellant which generates an aerosol of the substance drug or active substance.

Inhalation devices (or apparatus) commonly used in inhalation treatments often needs an inhalation chamber. The use of an inhalation chamber has long been recognized to facilitate and improve the medication in a treatment by inhalation (aerotherapy), in particular for improving the distribution of therapeutic substances (medicament) in the bronchi and reduce deposits in the airways above, where they are responsible for side effects. Indeed, in the absence of such an inhalation chamber, the coordination between the activation of the inhaler and inspiration is paramount. However, this coordination is difficult to achieve for many patients, especially in children.

The inhalation chamber defines an internal volume in which the medicament is propelled by means of an opening made in one end of the opening chamber which is fitted on the source of the drug, for example a MDI. At another end of the inhalation chamber is another opening in communication with the patient's mouth through a connection means, generally a tubular part such as a mouthpiece that the patient may insert in his/her mouth directly. It is also possible to connect a face mask on the connection means, in particular in the case of devices for young children. The drug substance is propelled as a gas in the inhalation chamber for example by pressing the MDI. When the patient inhales through the mask or mouthpiece, the drug substance is transported into the lungs of the patient by an outflow from the inhalation chamber generated by the patient's inhalation.

However, it is not easy for the patient to verify that the inspiratory flow generated was efficient enough to inhale the full dose of drug substance or that the inhalation device works correctly. For example, if the inspiratory flow is too low or too strong, effective treatment may be compromised.

Inhalation devices including an inhalation chamber in which means of attesting to the good inhalation of the patient are known in the art. For example, there is an inhalation chamber in which a visible color means adjacent to an unidirectional inhalation valve moves according to the inspiratory flow. Such means provides a way to assess the passage of the inspiratory flow through the valve, however it does not measure the flow rate of inspiratory flow and eventually compare it to a reference value.

Therefore, it is an object of the present invention to provide a flow measuring apparatus which may be used for measuring the flow through a section of an inhalation apparatus. Also, it is an object of the present invention to provide an inhalation apparatus having a flow measuring apparatus for measuring flow through a section of the inhalation apparatus.

SUMMARY

According to an embodiment, there is provided a flow measuring apparatus for measuring a flow through a section of an inhalation apparatus, comprising:
    at least one set of Pitot tubes comprising a first Pitot tube longitudinally contacting a second Pitot tube, the set of Pitot tubes being configured for traversing entirely a lumen of the section of an inhalation apparatus;
    the first and second Pitot tube being respectively fluidly connected to a differential pressure sensor, for measuring a difference between a stagnation pressure and a static pressure within the flow measuring apparatus;
    the first Pitot tube comprising at least one opening facing a direction of the flow; and
    the second Pitot tube comprising at least one opening facing a direction opposed to the flow.

The first and the second Pitot tubes may be back to back.

The at least one opening facing a direction of the flow and the at least one opening facing a direction opposed to the flow are substantially coplanar along the longitudinal axis of the first and the second Pitot tubes.

The set of Pitot tubes may be streamlined, to reduce resistance of the set of Pitot tubes to the flow within the section of an inhalation apparatus.

The one of the first and the second Pitot tube may be for measuring a stagnation pressure, and the other of the first and the second Pitot tube may be for measuring a static pressure.

The first Pitot tube is for measuring a stagnation pressure, and the second Pitot tube may be for measuring a static pressure, or the first Pitot tube may be for measuring a static pressure, and the second Pitot tube is for measuring a stagnation pressure.

The flow measuring apparatus of any one of claims 1 to 4, wherein the at least one opening is a single opening, or two openings, or three openings, or four openings.

The at least one opening may be a circular opening, or a slot, or an oval opening, or a square opening, or a rectangular opening, or combinations thereof.

The at least one opening may be positioned along the longitudinal axis of the first or second Pitot tubes at regular intervals.

The flow measuring apparatus may further comprise a processor, operatively connected to the flow measuring apparatus, for calculating the flow rate from the difference between a stagnation pressure and a static pressure measured with the flow measuring apparatus.

The flow measuring apparatus may further comprise a transmission means for transmitting the flow rate.

The flow measuring apparatus may further comprise a visual means to visually indicate correct use of the flow measuring apparatus, the inhalation apparatus, or both.

The any one of the processor, the transmission means, and the visual means may be comprised within a housing.

The set of Pitot tubes may be removable.

According to another embodiment, there is provided an inhalation apparatus for drug delivery by inhalation comprising:
an inhalation chamber having
a first end to be connected to a source of drug to be administered by inhalation to a user,
a second end to be connected to the user;
a flow measuring apparatus of the present invention, traversing entirely a lumen of a section of the inhalation apparatus, for measuring flow of the drug within the section of the inhalation apparatus.

The second end may be a mouthpiece or a tube to be connected to a face mask.

The inhalation apparatus may further comprise a valve, downstream of the inhalation chamber and upstream of the second end, allowing passage of the flow from the inhalation chamber to the second end.

The valve may be a one-way inhalation valve.

The second end may further comprise an expiratory valve.

The second end may further comprise a tubular portion.

The tubular portion may comprise an expiratory valve.

The at least one set of Pitot tubes may be provided in the first end, or in the inhalation chamber, or in the second portion, or combinations thereof to measure the inhalation flow rate.

The at least one set of Pitot tubes may be provided in the tubular portion, or the expiratory valve, or combinations thereof to measure the expiratory flow rate.

The flow measuring apparatus may be removable.

The following terms are defined below.

The term "Pitot tube" is intended to mean a pressure measurement instrument used to measure fluid flow velocity. It is used to measure liquid, air and gas velocities in the present invention. The Pitot tube is used to measure the local velocity at a given point in the flow stream and not the average velocity in the pipe or conduit.

The term "dynamic pressure" is intended to mean the kinetic energy per unit volume of a fluid particle. In simplified cases, the dynamic pressure is equal to the difference between the stagnation pressure and the static pressure.

The term "static pressure" is intended to mean the pressure of a fluid particle on a body when the body is at rest relative to the fluid.

The term "stagnation pressure" is the static pressure at a stagnation point in a fluid flow. At a stagnation point the fluid velocity is zero and all kinetic energy has been converted into pressure energy (isentropically). Stagnation pressure is equal to the sum of the free-stream dynamic pressure and free-stream static pressure. Stagnation pressure is sometimes referred to as Pitot pressure because it is measured using a Pitot tube.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
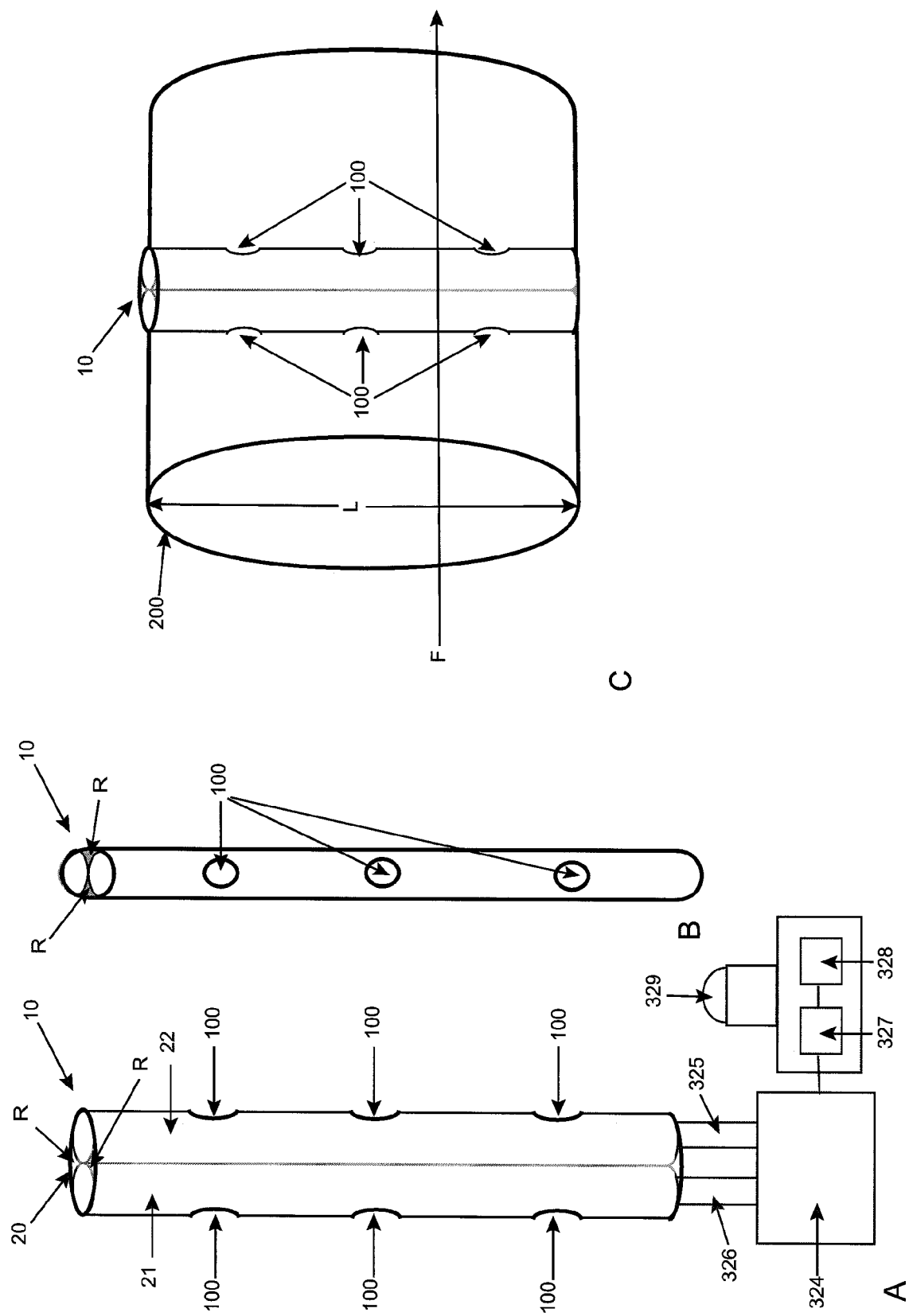
FIGS. 1A-C illustrates an embodiment of a flow measuring apparatus according to an embodiment of the present invention.

Referring now to the drawings, and more particularly to FIGS. 1A-C. In a first embodiments there is disclosed a flow measuring apparatus 10 for measuring a flow (F) through a section of an inhalation apparatus 200, which comprises:
at least one set of Pitot tubes 20 comprising a first Pitot tube 21 longitudinally contacting a second Pitot tube 22, the set of Pitot tubes 20 configured for traversing entirely a lumen (L) of the section of an inhalation apparatus 200;
the first and second Pitot tube 21, 22 are respectively fluidly connected to a differential pressure sensor 324, for measuring a difference between a stagnation pressure and a static pressure within the flow measuring apparatus 10;
the first Pitot tube 21 comprising at least one opening facing a direction of the flow (F); and
the second Pitot tube 22 comprising at least one opening facing a direction opposed to the flow (F).

Figure 9:
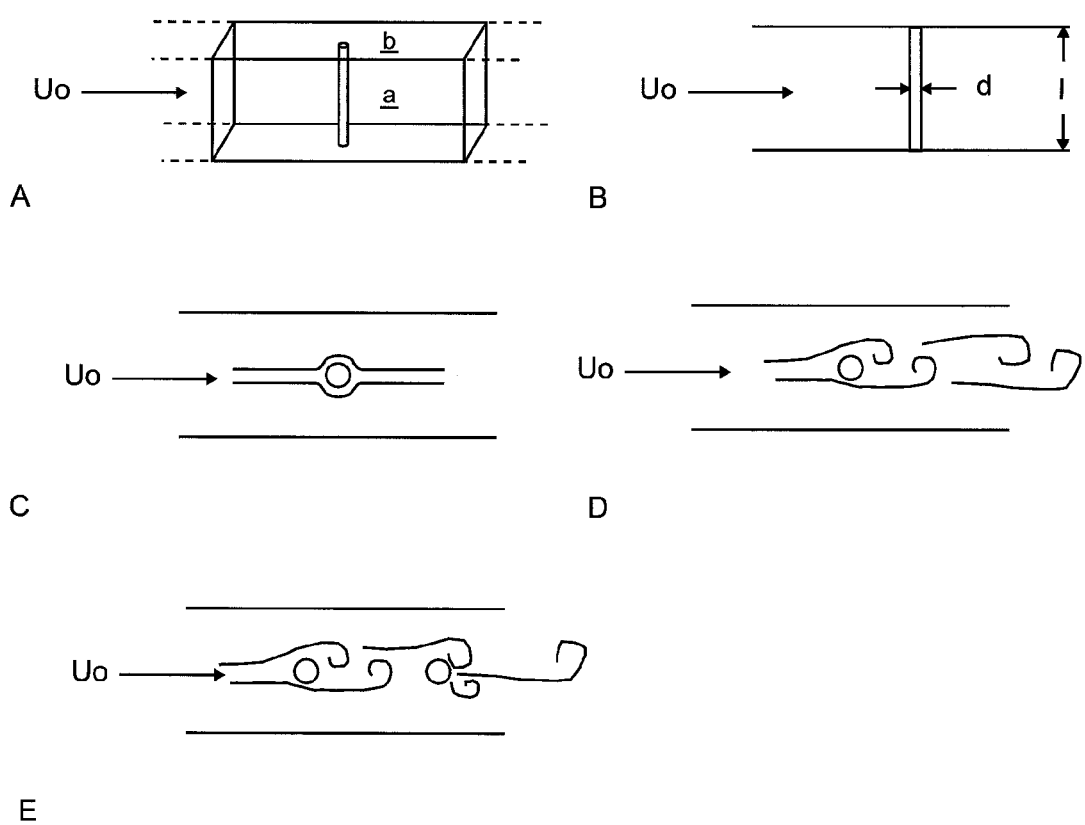
FIG. 9 illustrates schematically the flow under various scenario described herein.

Now referring to FIG. 9, the reference pattern usually considered as part of fluid mechanics is that of the wake formed downstream of a cylinder. The main flow in a conduit of rectangular section with sides a and b and a cylinder centered from wall to wall (diameter d and length l) (FIGS. 9A and B). The aspect ratio (l/d) of the cylinder is considered large (order of magnitude greater than 20, . . . 100).

The Reynolds number $$Re = \frac{U_o \cdot d}{v}$$

is defined with the flow velocity $U_0$. As a function of the increase of this dimensionless number, the organization of the flow changes dramatically.

Low Renolds numbers correspond to flow that is completely "laminar" while fully "turbulent" flows (FIGS. 9C and D, respectively) have high Renolds number. The turbulence is extended to all parts of the flow. For Renolds numbers ranging from 1000 to 10000 the presence of a wake is observed, where once the vortices formed in the vicinity of the downstream cylinder, they escape in alternance. The flow is essentially two-dimensional in the plane coinciding with the cylinder section. The vortices are periodic and consistent.

Other variations are discussed in the literature: the case of cylinders of small aspect ratio (short cylinders); the case where the cylinder does not cover the entire length of the test section, at the end of the cylinder, the organization of the flow becomes three-dimensional flow; and the case of tandem cylinders, where a second cylinder is placed farther downstream in the wake of the first, the organization of the flow becomes highly complex (FIG. 9E). In the case of the flow measuring apparatus 10 of the present invention, the conduit is not of rectangular section but of circular section, the flow is axy-symmetrical and not two dimensional.

Without wishing to be bound by theory, independently of the shape of the cross sections of the cylinders, they generate a wake. According to an embodiment of the present invention, the configuration of the flow measuring apparatus 10 of the present invention with a set of Pitot tubes 20 having a streamlined profile (e.g. having a section close to an oval shape), traversing the entire width of the conduit (the lumen of the conduit), results in principle in a flow having an organization likely to be at least two-dimensional on the central portion of the conduit. This therefore improves the precision and the reproducibility of the measurements, especially in situations where the flow is low.

Figure 7:
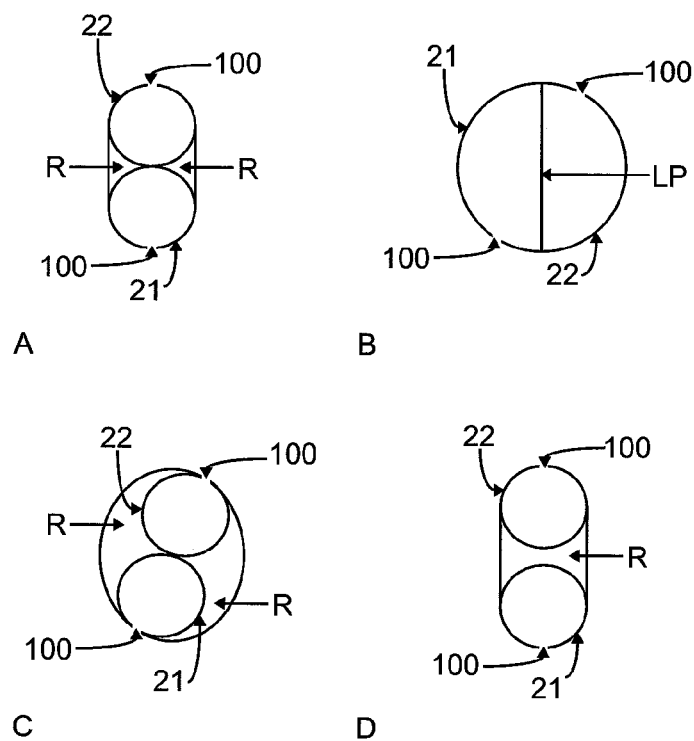
FIG. 7A-D illustrates embodiments of the set of Pitot tubes according to an embodiment of the present invention.

According to an embodiment, the set of Pitot tubes 20 may comprise first and second Pitot tubes 21, 22 which are contacting each other along the longitudinal axis to eliminate any gap between the first and second Pitot tubes 21, 22. Now referring to FIGS. 7A-D, in embodiments, the contact between the first and second Pitot tubes 21, 22 may be achieved in several manners. According to an embodiment, the first and second Pitot tubes 21, 22 may be back to back, resulting in their respective opening being substantially in the same plane (or in other words, coplanar along the longitudinal axis of the first and second Pitot tubes 21, 22), directly in contact with one another (FIG. 7A), with or without streamlining (as shown by the filling of the region "R" in FIGS. 7A, C and D). According to another embodiment, the set of Pitot tubes 20 may be comprised of two Pitot tubes 21, 22 contacting each other in a decentered manner, causing their respective openings to be in different planes. For example, each Pitot tubes 21, 22 may be a half-circle contacting the other along their linear portion LP (FIG. 7B), or two Pitot tubes 21, 22 may contact each other along their circumference, but not in a direct back to back manner (FIG. 7O). According to another embodiment, the Pitot tubes 21, 22 may contact each other by eliminating the region "R" between each tube, either by filling the gap between them, or preparing the set of Pitot tubes 20 as a unitary part (FIG. 7D). Preferably, the first and second Pitot tubes 21, 22 are back to back. The contact between the first and second Pitot tubes 21, 22 improves the precision and the reproducibility of the measurements, especially in situations where the flow is low. Furthermore, without wishing to be bound by theory, it is believed that the contact between the first and second Pitot tubes 21, 22 also reduces the turbulence in three dimensions near the flow measuring apparatus 10, limiting them to two dimensions, which again improves the precision and the reproducibility of the measurements.

Figure 2:
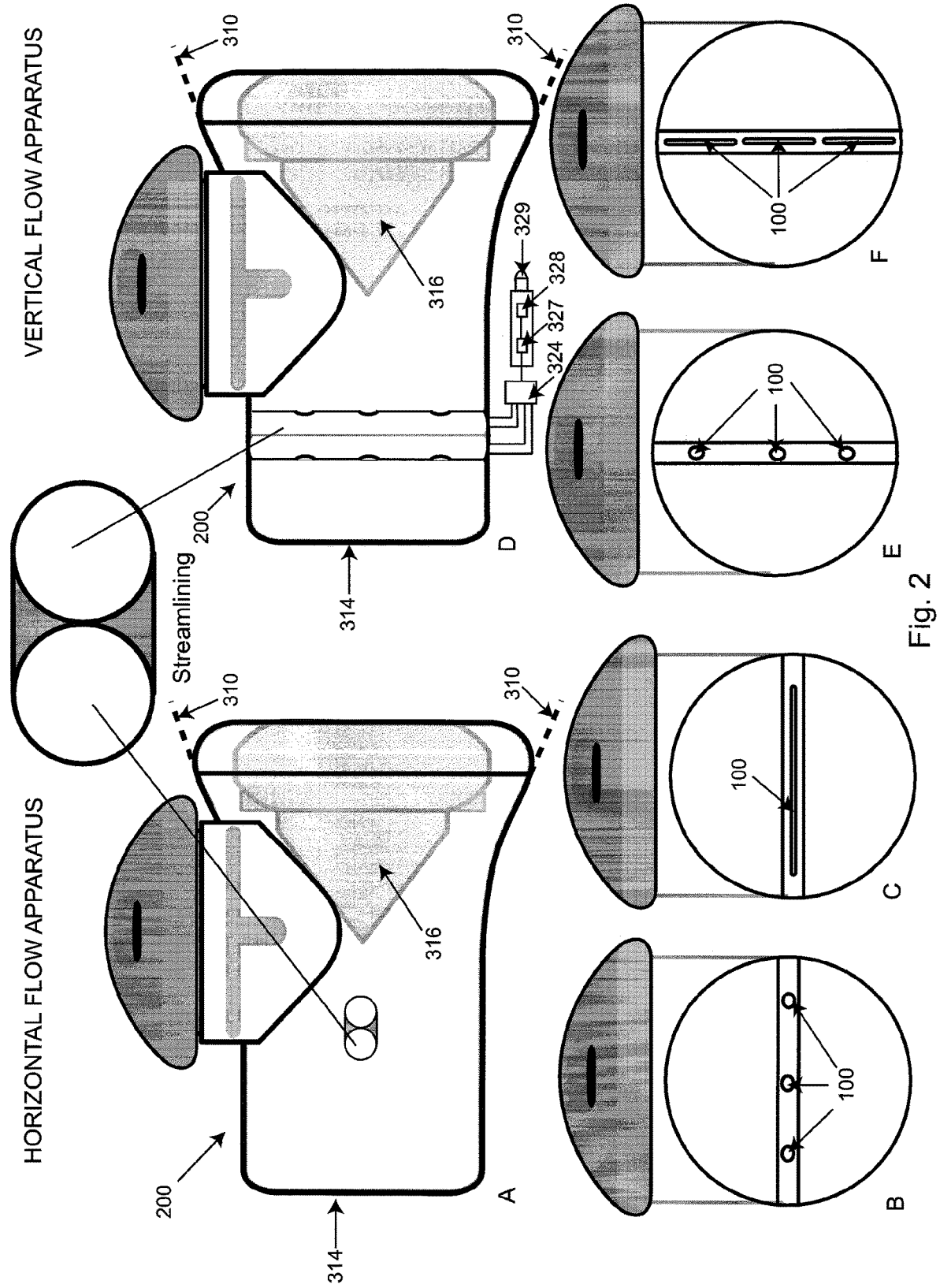
FIGS. 2A-F illustrates an embodiment of a flow measuring apparatus in an inhalation apparatus according to an embodiment of the present invention.

One of the Pitot tubes of the set 20 is a tube measuring stagnation pressure (e.g. first Pitot tube 21), the other is a measuring tube for static pressure (e.g. second Pitot tube 22). Each Pitot tube has at least one opening, such as opening 100. These openings allow the measurement of a mean stagnation pressure and a mean static pressure during the passage of a flow through the openings. Thus, according to an embodiment, the first and second Pitot tubes 21, 22 may comprise at least one opening 100 facing a direction of the flow (F). The at least one 100 opening may be a single, longitudinal opening slot, as shown in FIG. 2C. According to another embodiment, the at least one opening may be two, three, four, or more openings, such as circular openings (FIGS. 2B and E), or slots (FIG. 2F), positioned along the longitudinal axis of the first or second Pitot tubes 21, 22 at regular intervals. According to another embodiment, the at least one opening is distributed along the entire length of the Pitot tube. According to another embodiment, when more than one opening are present, the opening are distributed equally (at regular internals) along the length of the Pitot tube. Distribution along the length of the Pitot tube allows the flow to be measure at different positions in the lumen (e.g. in the center, and/or near the wall of the section of an inhalation apparatus).

According to another embodiment, the set of Pitot tubes 20 is configured for traversing entirely the lumen (L) of the section of an inhalation apparatus 200, as shown in FIG. 1C, and FIG. 2D. Fluid flowing through a tubular structure flows more rapidly in the center of the structure than around the edges of the structure. Therefore, the fact that the set of Pitot tubes 20 traverses the entire lumen (L) of the section of the inhalation apparatus 200, combined with having a single longitudinal slot, or a series of several openings at regular intervals along the length of the first or second Pitot tubes 21, 22, allows the measurements of the pressure to be made at several points of the lumen (L), particularly in the center and at the edges of the lumen, and permits averaging the pressure measurement and improves the precision and the reproducibility of the measurements, especially under low flow.

According to another embodiment, the set of Pitot tubes 20 may be streamlined in order to reduce the resistance of the set of Pitot tubes 20 to the flow within the section of an inhalation apparatus 200. According to an embodiment, the first and second Pitot tubes 21, 22 may be shaped so as to present a generally streamlined configuration when in contact with one another. For example, the first and second Pitot tubes 21, 22 may be shaped as half-circles, or half-ovals providing a substantially circular or oval shape to the set of Pitot tubes 20 when in contact with one another. According to another embodiment, the region (R) of the set of Pitot tubes 20 where the first and second Pitot tubes 21, 22 are in contact with one another may be filled with an appropriate material that is shaped or molded so as to provide a generally streamlined profiled (FIGS. 1A and B). According to another embodiment, the first and second Pitot tubes 21, 22 may be inserted into another tube, which then provides the desired streamlining (i.e. a streamlining tube). The so called streamlining tube also includes opening aligning with the openings of the Pitot tubes. According to another embodiment, the set of Pitot tubes 20 may be made from a unitary piece of material prepared from techniques such as injection molding, 3D printing, or machining. The unitary piece may be streamlined according to the present invention and include therein two longitudinal tube-like cavity corresponding to Pitot tubes 21, 22. Appropriate materials include but are not limited to plastic materials, metallic materials, etc.

According to another embodiment, the first and second Pitot tube 21, 22 are respectively fluidly connected to a differential pressure sensor 324, for measuring a difference between a stagnation pressure and a static pressure within the flow measuring apparatus 10.

The first and second Pitot tubes 21, 22 may be connected to the differential pressure sensor 324 through connecting means 325 and 326. According to another embodiment, the flow measuring apparatus 10 may also include a processor 327, for calculating the flow from the difference between a stagnation pressure and a static pressure measured with the flow measuring apparatus 10. The processor 327 may transmit a flow rate signal through transmission means 328 and/or a activate visual means 329, such as a light emitting diode, or a display, indicating the correct use of an inhalation apparatus, such as apparatus 200. The operation of these elements is described in FIG. 6.

Figure 3:
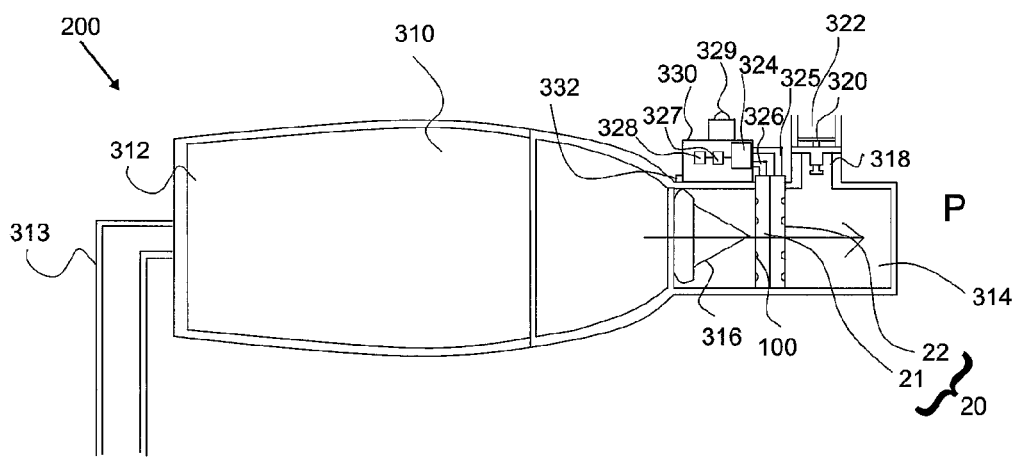
FIG. 3 illustrates an embodiment of a flow measuring apparatus in an inhalation apparatus according to an embodiment of the present invention.
Figure 4:
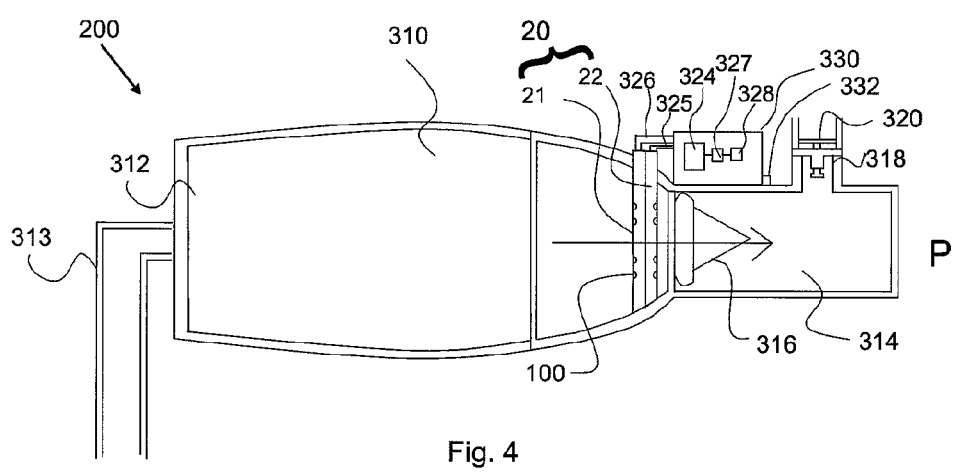
FIG. 4 illustrates an embodiment of a flow measuring apparatus in an inhalation apparatus according to an embodiment of the present invention.
Figure 5:
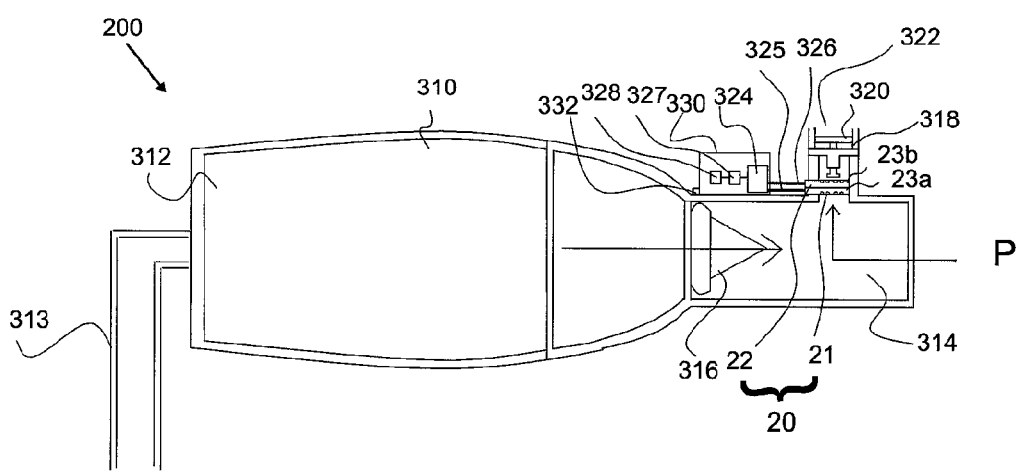
FIG. 5 illustrates an embodiment of a flow measuring apparatus in an inhalation apparatus according to an embodiment of the present invention.

The differential pressure sensor 324, the processor 327, the transmission means 328 and visual means 329 may be contained within a single housing 330 (FIGS. 3, 4 and 5). The Housing 330 may be removably attached on the outer face of an inhalation apparatus 200. For example, it may be removable attached through connection means 332, such as a snap connection means (FIGS. 3-5). According to another embodiment, the flow measuring apparatus 10 may be totally separable from the other elements of the inhalation apparatus 200, making it easier to clean the latter. According to another embodiment, the set of Pitot tube 20 may be removable to be replaced with a fresh part, or to be cleaned.

According to another embodiment, portions of the inhalation apparatus 200 may be removable, for example to be cleaned or to be replaceable by fresh part.

The same flow measuring apparatus 10 can comprise more than one sets of Pitot tubes 20. For example, a set of Pitot tubes 20 may be provided in the first end 312 of an inhalation apparatus 200 in order to measure the inhalation flow rate (FIG. 4), and another set of Pitot tubes 20 may be provided in the second end 314, and/or in the tubular portion 318 of an inhalation apparatus 200 (FIG. 5) that contains the expiratory valve 320 to measure the rate of expiratory flow (FIGS. 3-5). The flow measure can be performed in the first end 312 as well as in the second end 314 (according to the formula $Q=m^3/s$).

According to another embodiment, a flow measuring apparatus 10 of the present invention may be provided in an inhalation apparatus 200 without inspiratory or expiratory valves.

Figure 8:
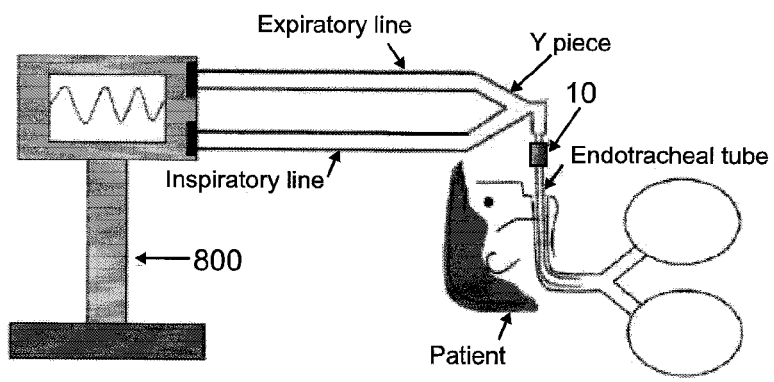
FIG. 8 illustrates schematically the use of an inhalation apparatus according to an embodiment of the present invention in a ventilation circuit.

Now referring to FIG. 8, according to another embodiment, the flow measuring apparatus 10 of the present invention may be provided in the ventilation circuit of a ventilator 800, allowing the medical practitioner to have independent data to compare to the data of the ventilator.

In a second embodiment there is disclosed an inhalation apparatus 200 for drug delivery by inhalation comprising:
an inhalation chamber 310 having a first end 312 to be connected to a source of drug to be administered by inhalation to a user (for example tubing or channel 313), and a second end 314 to be connected to the user;
a flow measuring apparatus 10 of the present invention, traversing entirely a lumen of a section of the inhalation apparatus 200, for measuring the drug flow within the section of the inhalation apparatus 200; and
a processor 327, operatively connected to the flow measuring apparatus, for calculating the flow rate from the difference between a stagnation pressure and a static pressure measured with the flow measuring apparatus 10.

According to the second embodiment, the inhalation chamber 310 having a first end 312 to be connected to a source of drug is intended to be the source of drug (in other words medicinal substances or medicaments) such as a spray inhaler or metered dose inhaler (MDI), and a second end 314, such as a connecting portion to be connected to the a user. This allows the communication between the inhalation chamber 310 of the inhalation apparatus 200 and thus a user. According to an embodiment, second end 314, such as the connecting portion may be either a mouthpiece or a tube that may be connected to a face mask.

According to another embodiment, the inhalation apparatus 200 may comprise a valve 316, for example a duckbill valve may be provided upstream of the user relative to the chamber 310. Any suitable valve may be used in the inhalation apparatus of the present invention. According to an embodiment, this valve 316 is preferably a one-way inhalation valve allowing the passage of a flow carrying the drug particles from the interior of the chamber 310 towards the connecting portion of the second end 314 and the user during the inhalation phase generated by the user.

According to another embodiment, the second end 314 may also comprises a tubular portion 318, having an expiratory valve 320. Preferably, the expiratory valve 320 is a unidirectional valve. The expiratory valve 320 permits the passage of the air flow generated by the user during an expiration phase to an outlet 322 included in the tubular portion 318.

The inhalation apparatus 200 includes a flow measuring apparatus 10 of the present invention, traversing entirely a lumen of a section of the inhalation apparatus 200, for measuring flow of the drug within the section of the inhalation apparatus 200. The flow measuring apparatus 10 as described above may be arranged in the path of flow in the second end 314 downstream of the valve 316 (FIG. 3), and/or upstream of the valve 316 in the inhalation chamber 310 of the inhalation apparatus 200 (FIG. 4), and/or on the expiratory flow path through the tubular portion 318 (FIG. 5).

The first and second Pitot tubes 21, 22 may be connected to the differential pressure sensor 324 through connecting means 325 and 326. According to another embodiment, the flow measuring apparatus 10 may also include a processor 327, for calculating the flow from the difference between a stagnation pressure and a static pressure measured with the flow measuring apparatus 10. The processor 327 may transmit a flow rate signal 328 and/or a activate visual means 329, such as a light emitting diode, indicating the correct use of an inhalation apparatus, such as apparatus 200. The operation of these elements is described in FIG. 6.

Figure 6:
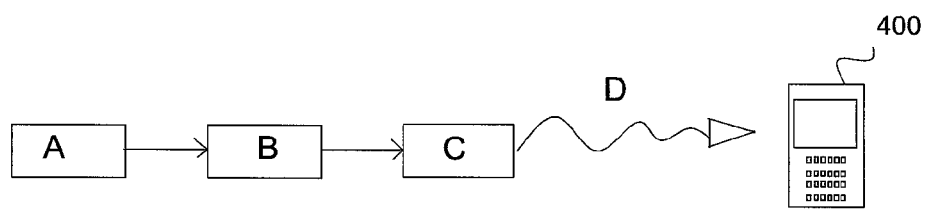
FIG. 6 illustrates schematically the functioning of an inhalation apparatus according to an embodiment of the present invention.

Now referring to FIG. 6, the difference between the static pressure and stagnation pressure average which are detected by the first and second Pitot tubes 21, 22 in the section of an inhalation apparatus 200 concerned is measured by the differential pressure sensor 324, which then delivers a pressure signal differential (step A). The processor 327 receives the pressure signal and calculates the flow rate (step B). The transmission means 328 transmits the signal flow delivered by the processor 327 to an external device 400, such as a portable machine equipped with a Bluetooth system or the likes (step D). This can be for example a cell phone, a tablet, etc. This allows the display on the external device 400 of either the flow value measured, or an indication to the user that a correct rate value and a proper functioning, or an incorrect rate value and an improper functioning of the inhalation apparatus 200. It is also possible to transmit a signal for the rate of drug delivery from the processor 327 to a visual means 329 attached to the inhalation apparatus 200 (step C). It may be for example a LED which illuminates when the value of the measured flow is the expected value or when on the contrary the value of the measured flow rate is less than a predetermined threshold value. This informs the user of the good operation of the inhalation apparatus 200 and the smooth running of the treatment.

The inhalation apparatus 200 may comprise a flow measuring apparatus 10 having more than one set of Pitot tubes 20. For example, a set of Pitot tubes 20 may be provided in the first end 312 of an inhalation apparatus 200 in order to measure the inhalation flow rate, and another set of Pitot tubes 20 may be provided in the tubular portion 318 that contains the expiratory valve 320 to measure the rate of expiratory flow. Also, more than one set of Pitot tubes 20 may be included in any one section of the inhalation apparatus.

According to another embodiment, a flow measuring apparatus 10 of the present invention may be provided in an inhalation apparatus 200 without inspiratory or expiratory valves.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. An inhalation apparatus comprising an inhalation chamber and a flow measuring apparatus in a section of the inhalation apparatus, the inhalation chamber receiving a metered-dose inhaler, and comprising a valve opposed to the metered-dose inhaler, the flow measuring apparatus for measuring a flow rate of gas comprising an aerosol through the section of the inhalation apparatus, the flow measuring apparatus comprising:
a set of Pitot tubes only in a single longitudinal axis traversing a lumen of the inhalation apparatus and comprising a first Pitot tube longitudinally aligned with and contacting a second Pitot tube,
said set of Pitot tubes traversing entirely the lumen of said section of the inhalation apparatus only in the single longitudinal axis;
said first and second Pitot tube being respectively fluidly connected to a differential pressure sensor, for measuring a difference between a stagnation pressure and a static pressure within said flow measuring apparatus;
said first Pitot tube comprising at least one opening facing a direction of said flow; and
said second Pitot tube comprising at least one opening facing a direction opposed to said flow;
wherein the set of Pitot tubes is in the section of the inhalation apparatus which is located downstream of the inhalation chamber, adjacent to the valve to measure the flow rate of the gas comprising the aerosol through the valve between the inhalation chamber and a mouthpiece, wherein the valve is a duckbill valve and defines a plane of a laminar flow for the flow of the gas comprising the aerosol, and the set of Pitot tubes crosses the flow of the gas comprising the aerosol with the single longitudinal axis thereof being perpendicular to the plane.

2. The inhalation apparatus of claim 1, wherein said first and said second Pitot tubes are back to back.

3. The inhalation apparatus of claim 2, wherein said at least one opening facing a direction of said flow and said at least one opening facing a direction opposed to said flow are substantially coplanar with longitudinal axes of said first and said second Pitot tubes, which are parallel.

4. The inhalation apparatus of claim 1, wherein said set of Pitot tubes is streamlined, to reduce resistance of said set of Pitot tubes to said flow within said section of an inhalation apparatus.

5. The inhalation apparatus of claim 1, wherein said at least one opening of said first Pitot tube or of said second Pitot tube is a single opening, or two openings, or three openings, or four openings.

6. The inhalation apparatus of claim 1, wherein said at least one opening of said first Pitot tube or of said second Pitot tube is a circular opening, or a slot, or an oval opening, or a square opening, or a rectangular opening, or combinations thereof.

7. The inhalation apparatus of claim 1, wherein said at least one opening of said first Pitot tube or of said second Pitot tube comprises a plurality of openings positioned along the longitudinal axis of the first or second Pitot tubes at regular intervals.

8. The inhalation apparatus of claim 1, further comprising a processor, operatively connected to said flow measuring apparatus, for calculating said flow rate from said difference between the stagnation pressure and the static pressure measured with said flow measuring apparatus.

9. The inhalation apparatus of claim 8, further comprising a transmission means for transmitting said flow rate.

10. The inhalation apparatus of claim 9, further comprising a visual means to visually indicate correct use of said flow measuring apparatus, said inhalation apparatus, or both.

11. The inhalation apparatus of claim 10, wherein any one of said processor, said transmission means, and said visual means is comprised within a housing.

12. The inhalation apparatus of claim 1, wherein said set of Pitot tubes is removable from the inhalation apparatus.

13. The inhalation apparatus of claim 1, wherein the inhalation apparatus is for drug delivery by inhalation,
the inhalation chamber having:
a first end to be connected to a source of drug to be administered by inhalation to a user, and
a second end to be connected to said user;
the flow measuring apparatus being for measuring flow of said drug within said section of said inhalation apparatus.

14. The inhalation apparatus of claim 13, wherein said second end is the mouthpiece or a tube to be connected to a face mask.

15. The inhalation apparatus of claim 13, wherein the inhalation chamber comprises the valve which is upstream of said second end, allowing passage of said flow from said inhalation chamber to said second end.

16. The inhalation apparatus of claim 15, wherein said valve is a one-way inhalation valve.

17. The inhalation apparatus of claim 13, wherein said second end further comprises an expiratory valve.

18. The inhalation apparatus of claim 17, wherein said second end further comprises a tubular portion.

19. The inhalation apparatus of claim 1, wherein the inhalation apparatus comprises the mouthpiece, downstream of the inhalation chamber, and the set of Pitot tubes traverses entirely a lumen of said mouthpiece only in the single longitudinal axis.

20. The inhalation apparatus of claim 19, wherein the duckbill valve is at an end of the inhalation chamber and extends toward the mouthpiece.

* * * * *